US00PP29945P2

(12) United States Plant Patent
Van Swieten

(10) Patent No.: US PP29,945 P2
(45) Date of Patent: Dec. 4, 2018

(54) ***PHALAENOPSIS* ORCHID PLANT NAMED 'PHALOSZIH'**

(50) Latin Name: ***Phalaenopsis* hybrid**
Varietal Denomination: PHALOSZIH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,845

(22) Filed: Aug. 14, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALOSZIH', particularly characterized by having purple flowers with a broad, lighter purple edge, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALOSZIH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALOSZIH'.

The new *Phalaenopsis* plant is a product of a planned breeding program conducted by the inventor in Bleiswijk, The Netherlands. The objective of this breeding program was to create a new *Phalaenopsis* plant with numerous attractive and unique purple flowers with a broad, lighter purple edge, suitable for potted plant production.

The new *Phalaenopsis* plant 'PHALOSZIH' is a result of cross-pollination made by the inventor in October 2007 in Bleiswijk, The Netherlands of the proprietary female, or seed parent, *Phalaenopsis* hybrid 'unknown' (unpatented) with the proprietary male, or pollen parent, *Phalaenopsis* hybrid 'unknown' (unpatented). At the time of the crossing the parent plants were known. However, due to a migration of information systems, the original crossing data cannot be determined with certainty. Therefore, the parents are considered to be unknown and no comparison with the female or male parents can be made.

The new *Phalaenopsis* was selected by the inventor as a single plant within the progeny of the stated cross-pollination in a controlled greenhouse in Bleiswijk, The Netherlands in October 2010. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALOSZIH' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALOSZIH' as a new and distinct variety of *Phalaenopsis* plant.

1) Purple flowers with a broad, lighter purple edge;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in May 2017. Colors in the photographs may differ from the color values cited in the detailed botanical description, which accurately describe the actual colors of the new variety.

DESCRIPTION OF THE NEW VARIETY

Figure 1:
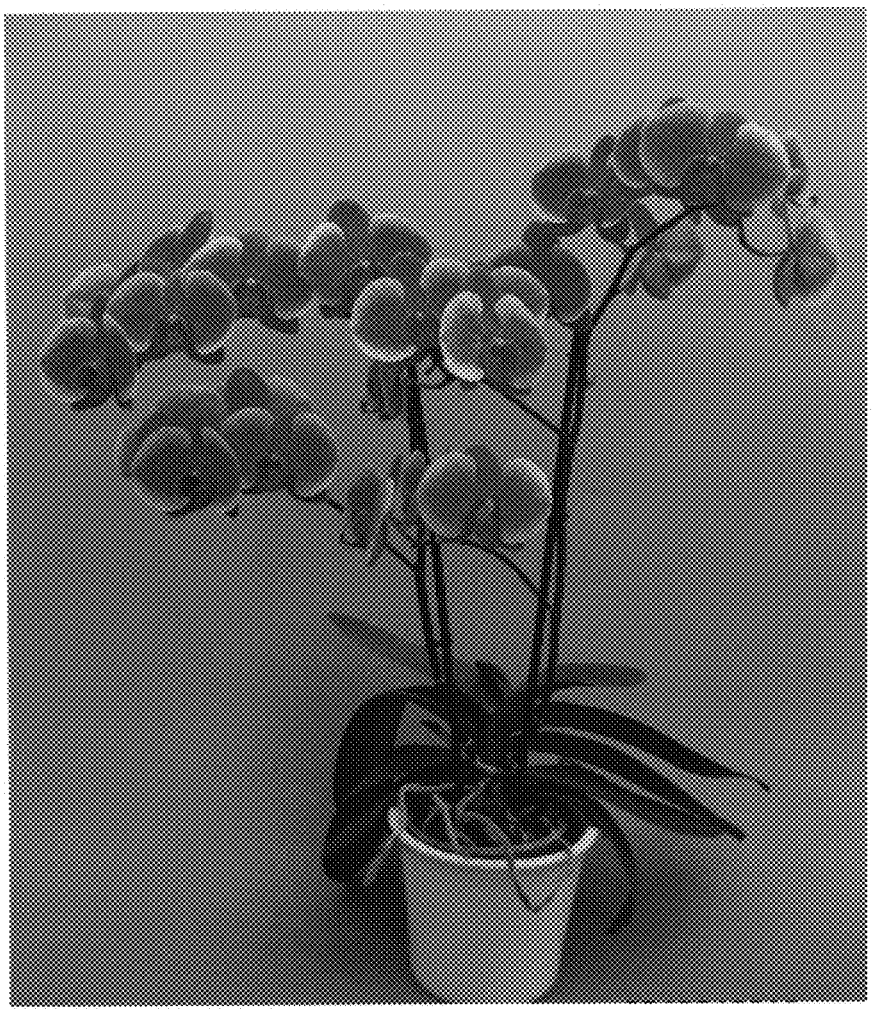
FIG. 1 shows the overall plant habit, including blooms and foliage of 'PHALOSZIH'.
Figure 2:
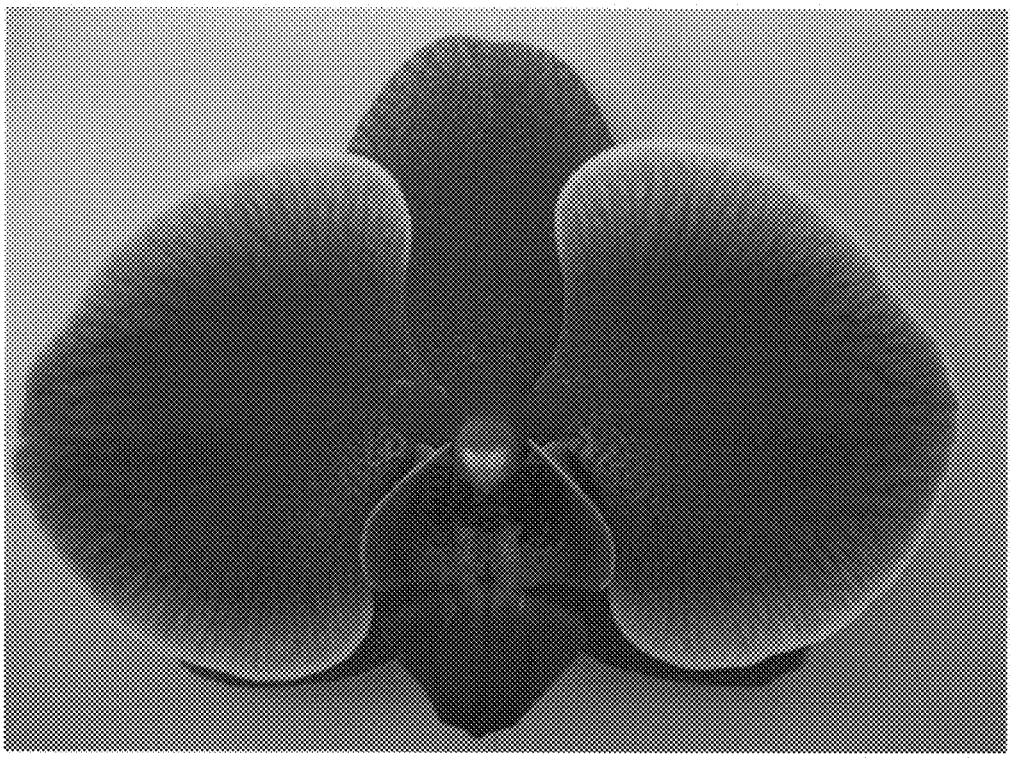
FIG. 2 shows a close-up of a flower of 'PHALOSZIH'.
Figure 3:
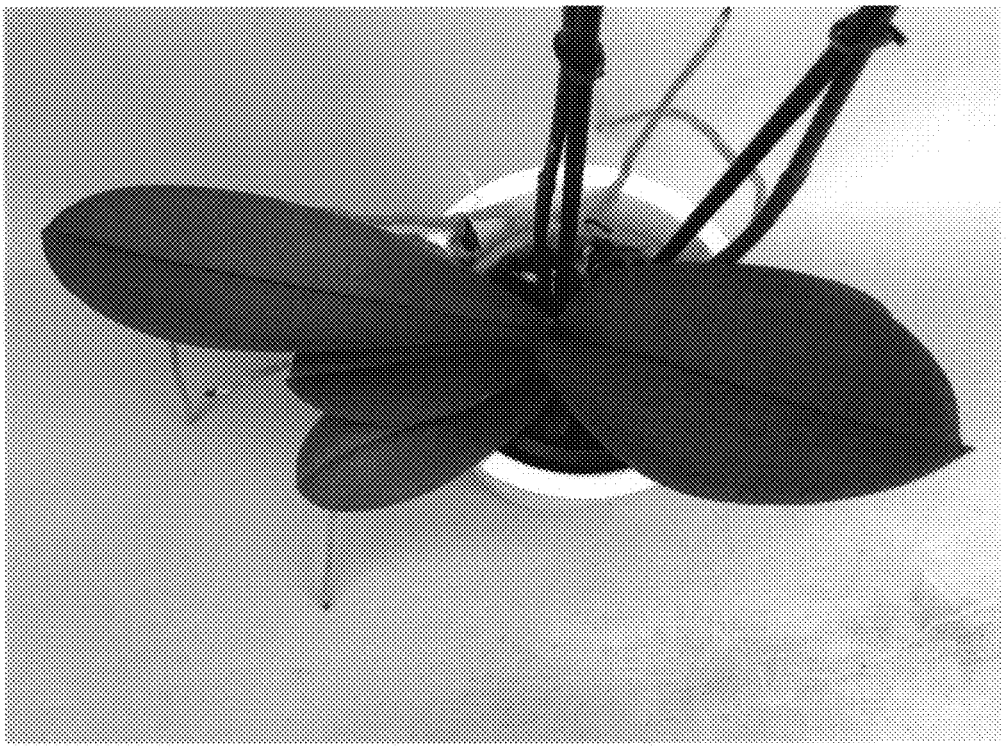
FIG. 3 shows a close-up of the leaves of 'PHALOSZIH'.

The following detailed description sets forth the distinctive characteristics of 'PHALOSZIH'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALOSZIH'.

Parentage:

*Female parent*.—*Phalaenopsis* cultivar 'unknown' (unpatented).

*Male parent*.—*Phalaenopsis* cultivar 'unknown' (unpatented).

Propagation:

*Type*.—Meristem tissue culture.

Roots:

*Root description*.—Greyed-green colored roots (RHS 190B/C) with branching lateral roots having red-purple colored root tips (RHS N79B/C).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height (from soil level to top of inflorescence)*.—Approximately 39.0 cm to 49.0 cm.

*Width (measured from leaf tips)*.—About 31.0 cm to 33.0 cm.

*Vigor*.—Moderate.

Leaves:

*Mature leaves*.—Quantity per plant: 6 to 8 leaves are produced before flowering. Length (fully expanded): 17.0 cm to 19.0 cm. Width: 7.0 cm to 8.0 cm. Shape: Oblong. Base shape: Moderately elongated. Apex: Obtuse unequal. Leaf blade angle with the petiole (measured from the horizontal position): Between 20 degrees and 35 degrees. Leaf margin: Entire. Color: Upper surface: RHS 147A. Lower surface: RHS 147B and 187A. Texture: Rough. Thickness: 2.5 mm to 2.8 mm. Venation: Pattern: Parallel. Color of the midvein: Upper surface: RHS 187A and 147A. Lower surface: RHS 187A.

Peduncle:

*Quantity per plant*.—1 to 3.

*Number of flowers per peduncle*.—8 to 15.

*Length*.—39.0 cm to 49.0 cm.

*Diameter*.—4.8 mm to 5.3 mm.

*Strength*.—Moderate.

*Aspect*.—Upright to slightly pendant.

*Texture*.—Smooth.

*Color*.—Mix of brown (RHS 200A) and green (RHS 147B).

*Internode length*.—3.0 cm to 4.0 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 150.0 mm to 180.0 mm.

*Flowering time*.—First flowers can be expected 10 to 11 months after planting in a 12 cm (diameter) pot.

*Flower*.—Height: 70.0 mm to 75.0 mm. Diameter: 85.0 mm to 90.0 mm. Depth of lip: 21.0 mm to 23.0 mm.

*Flower longevity*.—On the plant: 8 to 12 weeks.

*Fragrance*.—Absent.

*Flower bud*.—Average size: Large. Length: 24.0 mm to 26.0 mm. Width: 20.0 mm to 22.0 mm. Shape: Egg shaped. Color: Purple-red (RHS N77B) and green (RHS 147C).

*Petals*.—Arrangement: Open/free. Shape: Semi-circular. Apex: Rounded asymmetric. Margin: Slightly undulated. Length (from base to tip): 40.0 mm to 42.0 mm. Width: 54.0 mm to 56.0 mm. Color (when fully opened): Upper surface: Basic color: Light purple (RHS 76B). Over color: Purple (RHS N78A). Lower surface: Basic color: Light purple (RHS 76B). Over color: Purple (RHS N78B).

*Dorsal sepal*.—Shape: Elliptic. Apex: Rounded to slightly emarginated. Margin: Entire. Length (from base to tip): 41.0 mm to 43.0 mm. Width: 28.0 mm to 30.0 mm. Color (when fully opened): Upper surface: Basic color: Purple (RHS N78A/B). Over color: Absent. Lower surface: Basic color: Purple (RHS N78B). Over color: Light purple (RHS 76A) and slightly light green (RHS 196B) in the middle.

*Lateral sepals*.—Shape: Ovate. Apex: Obtuse asymmetric. Margin: Entire. Length (from base to tip): 40.0 mm to 42.0 mm. Width: 24.0 mm to 26.0 mm. Color (when fully opened): Upper surface: Basic color: Purple (RHS N78B). Over color: Light green at the base (RHS 145D) and dark red (RHS 183A) spots. Lower surface: Basic color: Light purple (RHS 76A). Over color: Green (RHS 196B) at the base and purple stripe (RHS N78B) in the middle.

*Labellum (lip)*.—Whiskers: Present. Length of whiskers: 11.0 mm to 13.0 mm. Color of whiskers: Dark red (RHS 187A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 19.0 mm to 21.0 mm. Width: 15.0 mm to 17.0 mm. Color: Slightly yellow at the base (RHS 8B) with dark stripes (RHS 59A) on one side and purple along the edge (RHS 71A).

*Apical lobe*.—Shape: Triangular. Margin: Entire. Length: 19.0 mm to 21.0 mm. Width: 19.0 mm to 21.0 mm. Color: Slightly yellow (RHS 8B) and dark red (RHS 59A/B) at the base and purple (RHS N78A) toward the whiskers.

*Callus*.—Average size: Medium. Height: 0.5 cm to 0.7 cm. Length: 0.5 cm to 0.7 cm. Width: 0.4 cm to 0.6 cm. Color: Yellow (RHS 8B) dotted (RHS 178A).

Reproductive organs:

*Column*.—Length: 7.0 mm to 9.0 mm. Diameter: 5.1 mm to 5.4 mm. Color: Purple (RHS N78A/B).

*Pollinia*.—Quantity: 2. Diameter: 1.0 mm to 1.2 mm. Color: Orange (RHS 26A).

*Ovary*.—Length: 7.0 mm to 9.0 mm. Diameter: 2.4 mm to 2.6 mm.

*Pedicel*.—Length: 36.0 mm to 38.0 mm. Diameter: 3.1 mm to 3.3 mm. Color: Green at the base (RHS 147C) and purple (RHS N78D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL LINES AND MOST SIMILAR VARIETIES

The female and male parent plants of 'PHALOSZIH' are unknown, so a meaningful comparison cannot be made.

'PHALOSZIH' is most similar to the commercial *Phalaenopsis* plants named 'PHALDUKAI' (U.S. Plant Pat. No. 28,157) and 'PHALDANBO' (U.S. Plant Pat. No. 25,930). 'PHALOSZIH' differs from the commercial variety 'PHALDUKAI' in that 'PHALOSZIH' has flowers with a broad edge pattern, a slightly yellow apical lobe with dark red at the base and purple toward the whiskers, and a callus with yellow sides, whereas 'PHALDUKAI' has flowers with a center pattern, a dark red apical lobe and a callus with brown sides. Additionally, 'PHALOSZIH' has narrower dorsal sepals than 'PHALDUKAI'.

'PHALOSZIH' differs from the commercial variety 'PHALDANBO' in that 'PHALOSZIH' has flowers with a broad edge pattern, a slightly yellow apical lobe with dark red at the base and purple toward the whiskers and a medium-sized, yellow (RHS 8B) callus, whereas 'PHALDANBO' has flowers with a small edge pattern, a dark red apical lobe and a small, yellow (RHS 15A) callus. Additionally, 'PHALOSZIH' has narrower dorsal sepals than 'PHALDANBO'.

I claim:

1. A new and distinct variety of *Phalaenopsis* plant named 'PHALOSZIH', substantially as described and illustrated herein.

* * * * *